(12) United States Patent
Granados et al.

(10) Patent No.: US 11,022,377 B2
(45) Date of Patent: Jun. 1, 2021

(54) HEAT EXCHANGER COMPRISING A DEVICE FOR DISTRIBUTING A LIQUID/GAS MIXTURE

(71) Applicant: L'Air Liquide, Societe Anonyme pour l'Etude et l'Exploitation des Procedes Georges Claude, Paris (FR)

(72) Inventors: Ludovic Granados, Puteaux (FR); Philippe Grigoletto, Villeparisis (FR); Natacha Haik-Beraud, Champigny sur Marne (FR); Sophie Lazzarini, Saint Mande (FR); Jean-Marc Peyron, Creteil (FR); Eduard Rosa, Paris (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 296 days.

(21) Appl. No.: 16/312,078

(22) PCT Filed: Jun. 27, 2017

(86) PCT No.: PCT/FR2017/051709
§ 371 (c)(1),
(2) Date: Dec. 20, 2018

(87) PCT Pub. No.: WO2018/002509
PCT Pub. Date: Jan. 4, 2018

(65) Prior Publication Data
US 2019/0242651 A1    Aug. 8, 2019

(30) Foreign Application Priority Data
Jul. 1, 2016 (FR) .................................. 1656320

(51) Int. Cl.
*F28D 9/00*    (2006.01)
*G16H 10/40*    (2018.01)
*F25J 5/00*    (2006.01)
(Continued)

(52) U.S. Cl.
CPC .......... *F28D 9/0068* (2013.01); *F25J 1/0022* (2013.01); *F25J 1/0055* (2013.01); *F25J 1/0262* (2013.01);
(Continued)

(58) Field of Classification Search
CPC ............ F28D 9/0068; F28D 2021/0033; F25J 1/0022; F25J 1/0055; F25J 1/0262; F25J 5/002; F25J 2290/32
(Continued)

(56) References Cited

U.S. PATENT DOCUMENTS 3,559,722 A * 2/1971 Schauls ................. F28D 9/0068
                                                                                           165/166
3,880,231 A * 4/1975 Gauthier ............... F28D 9/0068
                                                                                           165/166
(Continued)

FOREIGN PATENT DOCUMENTS

| EP | 0 797 065 A2 | 9/1997 |
|----|--------------|--------|
| FR | 2 563 620 A1 | 10/1985 |
| GB | 2 127 140 A | 4/1984 |

OTHER PUBLICATIONS

International Search Report for corresponding PCT/FR2017/051709, dated Nov. 7, 2017.

*Primary Examiner* — Tho V Duong
*Assistant Examiner* — Raheena R Malik
(74) *Attorney, Agent, or Firm* — Justin K. Murray

(57) ABSTRACT

Heat exchanger with plates comprising a first series of passages for conducting at least one frigorigenic fluid and a second series of passages for conducting at least one calorigenic fluid, each passage being defined between two successive plates and extending parallel to a longitudinal axis, at least one mixing device arranged in at least one passage of the first series, said mixing device being configured to receive a liquid phase and a gaseous phase of the frigori- (Continued)

genic fluid and to distribute a mixture of said phases into said at least one passage. According to the invention, at least one passage of the second series adjacent to said at least one passage of the first series comprises a heat exchange structure divided in the longitudinal direction into at least a first portion and a second portion which are juxtaposed along the longitudinal axis, the second portion extending facing at least part of the mixing device, and being configured so as to present a heat exchange coefficient which is lower than the heat exchange coefficient of the first portion.

16 Claims, 5 Drawing Sheets

(51) Int. Cl.
*F25J 1/00* (2006.01)
*F25J 1/02* (2006.01)
*G06K 7/10* (2006.01)
*F28D 21/00* (2006.01)

(52) U.S. Cl.
CPC .......... *F25J 5/002* (2013.01); *G06K 7/10425* (2013.01); *G16H 10/40* (2018.01); *F25J 2290/32* (2013.01); *F28D 2021/0033* (2013.01)

(58) Field of Classification Search
USPC .......................................................... 165/166
See application file for complete search history.

(56) References Cited

U.S. PATENT DOCUMENTS

| | | | | |
|---|---|---|---|---|
| 3,895,676 A * | 7/1975 | Young | ...................... | F25J 5/002 165/167 |
| 3,992,168 A * | 11/1976 | Toyama | ............... | B01D 5/0015 165/166 |
| 4,249,595 A * | 2/1981 | Butt | ......................... | F25J 5/002 165/110 |
| 4,450,903 A * | 5/1984 | Butt | ....................... | B01D 1/221 165/110 |
| 4,646,822 A | 3/1987 | Linde | | |
| 4,715,431 A * | 12/1987 | Schwarz | ............... | F28D 9/0081 165/110 |
| 4,715,433 A * | 12/1987 | Schwarz | ............... | F25J 3/04412 165/110 |
| 5,122,174 A | 6/1992 | Sunder et al. | | |
| 5,709,264 A * | 1/1998 | Sweeney | ............... | F28D 9/0068 165/115 |
| 6,019,160 A * | 2/2000 | Chen | ..................... | F28D 19/044 165/10 |
| 6,634,419 B1 * | 10/2003 | Beldam | ................. | F28D 9/0068 165/146 |
| 7,163,051 B2 * | 1/2007 | Jibb | ........................ | F28F 9/026 165/110 |

* cited by examiner

HEAT EXCHANGER COMPRISING A DEVICE FOR DISTRIBUTING A LIQUID/GAS MIXTURE

CROSS REFERENCE TO RELATED APPLICATIONS

This application is a § 371 of International PCT Application PCT/FR2017/051709, filed Jun. 27, 2017, which claims the benefit of FR1656320, filed Jul. 1, 2016 all of which are herein incorporated by reference in their entireties.

TECHNICAL FIELD OF THE INVENTION

The present invention concerns a heat exchanger comprising series of passages for each of the fluids to be brought into a heat exchange relationship, the exchanger comprising at least one mixing device configured to distribute at least one two-phase liquid/gas mixture into one of the series of passages.

In particular, the present invention may be applied to a heat exchanger which vaporises at least one flow of a liquid/gas mixture, in particular a flow of a mixture with several constituents, for example a mixture of hydrocarbons, by exchange of heat with at least one other fluid, for example natural gas.

BACKGROUND OF THE INVENTION

The technology currently used for an exchanger is that of aluminium exchangers with brazed plates and fins, which leads to highly compact devices offering a large exchange surface area.

These exchangers comprise plates between which heat exchange wave structures are inserted; these structures are formed by a succession of wave legs or fins, thus constituting a stack of vaporisation passages and condensation passages, the first being intended for vaporising the frigorigenic fluid and the second for condensing a calorigenic gas. The heat exchanges between the fluids may take place with or without a change of phase.

In order to ensure the good function of an exchanger using a liquid/gas mixture, the proportion of the liquid phase and the gaseous phase must be the same in all passages and must be uniform within the same passage.

The dimensions of the exchanger are calculated by assuming a uniform distribution of phases, and hence a single temperature at the end of vaporisation of the liquid phase which is equal to the dew point temperature of the mixture.

For a mixture with several constituents, the vaporisation end temperature will depend on the proportion of the liquid phase and the gaseous phase in the passages.

In the case of an unequal distribution of the two phases, the temperature profile of the frigorigenic fluid will therefore vary between passages, or even vary within the same passage. Because of this non-uniform distribution, it may be that the calorigenic fluid or fluids in an exchange relationship with the two-phase mixture have a temperature at the outlet of the exchanger which is higher than the specified temperature, which consequently degrades the performance of the heat exchanger.

One solution for distributing the liquid and gaseous phases of the mixture as uniformly as possible consists of introducing them separately into the exchanger and then mixing them together only inside the exchanger.

Document FR-A-2563620 describes such an exchanger in which a mixing device, such as a grooved bar, is inserted in the series of passages intended to conduct the two-phase mixture. The mixing device comprises separate inlets for a liquid phase and a gaseous phase, opening into a common mixing volume equipped with an outlet for distributing the liquid/gas mixture towards the heat exchange zone.

However, the liquid phase supplying the mixing device is then inevitably in a situation of heat exchange with the calorigenic fluid or fluids circulating in the adjacent passages of the other series of passages. This may lead to a start of vaporisation of the liquid phase within the corresponding inlets, thus leading to an unequal distribution of the two phases of the mixture in certain passages of the series, and in certain zones within a same passage.

In order to minimise the heat exchanges which may occur at the mixing device, one solution would be to install the mixing device in a zone of the exchanger in which no other fluid is circulating. It would then be necessary to place the mixing device at one end of the exchanger where there is no means of fluid evacuation or supply, which would require restructuring of the exchanger as a whole and would necessarily lead to an increase in its size. Also, such a solution would not allow the introduction of the two-phase mixture into the middle of the exchanger, which may be desirable in cases where the specific features of the process require this.

SUMMARY OF THE INVENTION

The object of certain embodiments of the present invention is to solve all or some of the above-mentioned problems, in particular by proposing a heat exchanger in which the distribution of the liquid and gaseous phases of a mixture is as uniform as possible, without excessively complicating the structure of the exchanger or increasing its size.

The solution according to the invention is then a heat exchanger comprising:
  a plurality of plates arranged parallel to each other so as to define a first series of passages for conducting at least one frigorigenic fluid and a second series of passages for conducting at least one calorigenic fluid to be brought into a heat exchange relationship with at least said frigorigenic fluid, each passage being defined between two successive plates and extending parallel to a longitudinal axis, and
  at least one mixing device arranged in at least one passage of the first series, said mixing device being configured to receive a liquid phase and a gaseous phase of the frigorigenic fluid and to distribute a mixture of said phases into said at least one passage,
  wherein at least one passage of the second series adjacent to said at least one passage of the first series comprises a heat exchange structure divided along the longitudinal axis z into at least a first portion and a second portion which are juxtaposed along the longitudinal axis,
  the second portion extending facing at least part of the mixing device, and being configured so as to present a heat exchange coefficient which is lower than the heat exchange coefficient of the first portion.
  Depending on case, the exchanger of the invention may comprise one or more of the following technical characteristics:
    said first and second portions comprise respectively at least one first wave structure and at least one second wave structure, said first and second wave structures being juxtaposed along the longitudinal axis z and each having several wave fins connected alternately by wave peaks and by wave troughs succeeding each other in an undulation direction, the second wave structure extending facing at least part of the mixing device and being configured so as to present a heat exchange coefficient which is lower than the heat exchange coefficient of the first wave structure.

the second wave structure has a density which is lower than the density of the first wave structure, the density of each wave structure being defined as the number of wave fins per unit of length measured in the undulation direction.

the density of the second wave structure represents between 20% and 80%, preferably between 25% and 50% of the density of the first wave structure.

the density of the second wave structure is between 6 and 15 fins per inch (1 inch=2.54 centimetres).

said first and second portions are formed from strips, the second portion being formed from at least one strip with a thickness which is greater than the thickness of at least one strip forming said first wave structure of the portion.

the second wave structure is a straight wave, the first wave structure being selected from a straight wave, a straight perforated wave, a serrated wave, an undulating wave or a herringbone wave.

the second portion extends at least facing the entirety of the mixing device.

the second portion has a length parallel to the longitudinal axis of between 30 and 500 mm.

the heat exchange structure is furthermore divided along the longitudinal axis into a third portion, the second portion being configured so as to present a heat exchange coefficient which is less than or equal to the heat exchange coefficient of the third portion, the second portion being arranged between the first portion and the third portion.

the exchanger comprises first means for distributing or evacuating calorigenic fluid into or from said at least one passage of the second series of passages, and second means for distributing a liquid or gaseous phase of the frigorigenic fluid into said at least one passage of the first series towards the mixing device.

the mixing device comprises separate inlets for a liquid phase and a gaseous phase of the frigorigenic fluid, said separate inlets being connected fluidically via a common mixing volume to at least one outlet for a mixture of said liquid and gaseous phases.

the outlet for a two-phase liquid/gas mixture of the mixing device is situated along the longitudinal axis at a first position in said at least one passage of the first series, the second portion extending at least from the first position up to a second position situated between the first position and the first means for distributing or evacuating the calorigenic fluid.

the second portion extends up to the first means for distributing or evacuating the calorigenic fluid.

the second portion is formed by all or part of said first means for distributing or evacuating the calorigenic fluid.

The present invention may apply to a heat exchanger which vaporises at least one flow of a liquid/gas mixture, in particular a flow of a mixture with several constituents, for example a mixture of hydrocarbons, e.g. natural gas, by exchange of heat with at least one other fluid, e.g. natural gas.

The term "natural gas" refers to any compound containing hydrocarbons, including at least methane. This includes a "raw" compound (prior to any treatment or washing) and any compound which has been partially, substantially or entirely processed for the reduction and/or elimination of one or more components, including but not limited to sulphur, carbon dioxide, water, mercury and certain heavy and aromatic hydrocarbons.

BRIEF DESCRIPTION OF THE DRAWINGS

The present invention will be clearly understood and its advantages will arise from the description which follows, given merely as a non-limitative example, and with reference to the attached drawings in which.

DETAILED DESCRIPTION

Figure 1:
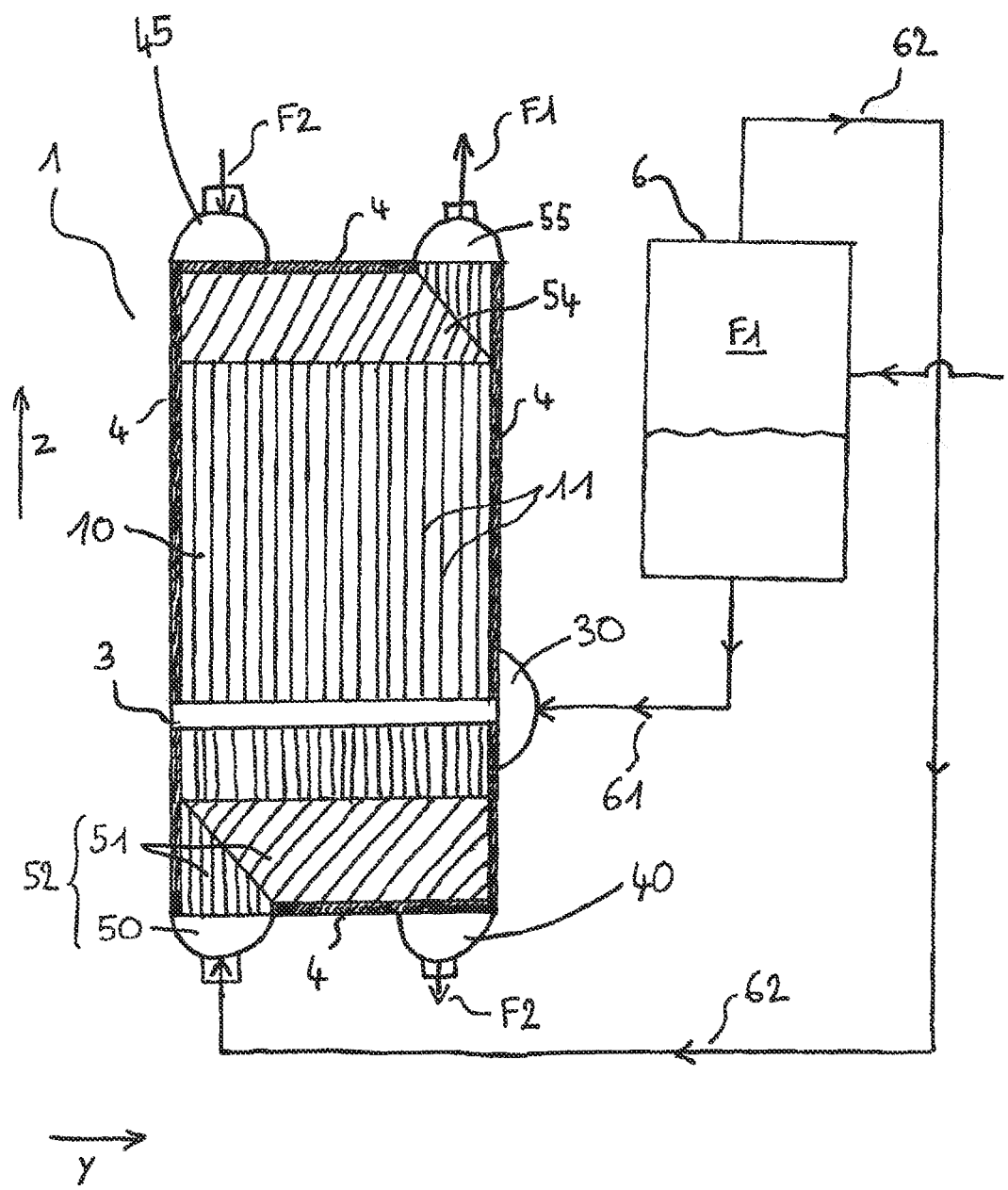
FIG. 1 is a diagrammatic cross-section view, in a plane parallel to the longitudinal and transverse axes, of part of a passage of a heat exchanger supplied with a two-phase liquid/gas mixture in accordance with the invention.

The heat exchanger 1 according to the invention comprises a stack of plates 2 extending in two dimensions of length and width, respectively following the longitudinal axis z and the lateral axis y. The plates 2 are arranged in parallel, one above the other with spacing, and thus form a plurality of passages for fluids in an indirect heat exchange relationship via the plates 2. The lateral axis y is orthogonal to the longitudinal axis z and parallel to the plates 2.

Preferably, each passage has a flat parallelepipedic form. The spacing between two successive plates is small in relation to the length and width of each successive plate.

The exchanger 1 may comprise a number of plates greater than 20, even greater than 100, defining between them a first series of passages 10 for conducting at least one frigorigenic fluid F1, and a second series of passages 20 (not shown on FIG. 1) for conducting at least one calorigenic fluid F2, said fluids generally flowing along the longitudinal axis z. The passages 10 of the first series may be arranged fully or partly alternately with or adjacent to all or part of the passages 20 of the second series.

In a manner known in itself, the exchanger 1 comprises distribution and evacuation means 42, 43, 52, 53 configured to distribute the different fluids selectively into the passages 10, 20, and to evacuate said fluids from said passages 10, 20.

The passages 10, 20 are generally sealed along the edges of the plates 2 by lateral and longitudinal sealing strips 4 fixed to the plates 2. The lateral sealing strips 4 do not fully block the passages 10, 20, but advantageously leave fluid inlet and outlet openings situated in diagonally opposing corners of the passages.

The openings of the passages 10 of the first series are arranged one above the other, while the openings of the passages 20 of the second series are arranged in opposite corners. The openings placed one above the other are connected respectively in collectors 40, 45, 50, 55 of semi-tubular form, via which the fluids are distributed and evacuated.

Figure 3:
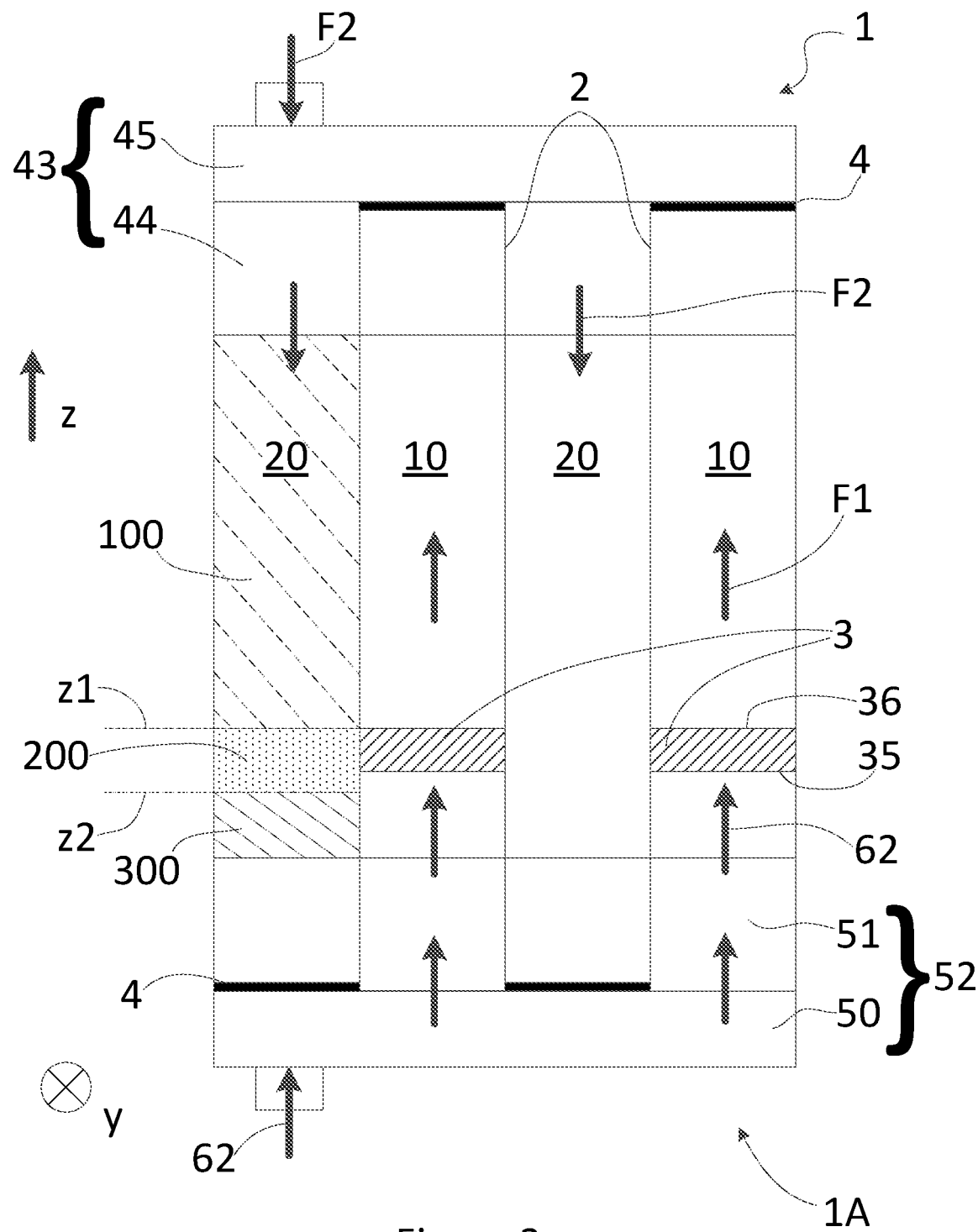
FIG. 3 is a diagrammatic cross-section view, in a plane parallel to the longitudinal axis and perpendicular to the lateral axis, of series of passages of the heat exchanger in FIG. 1 according to one embodiment of the invention.
Figure 4:
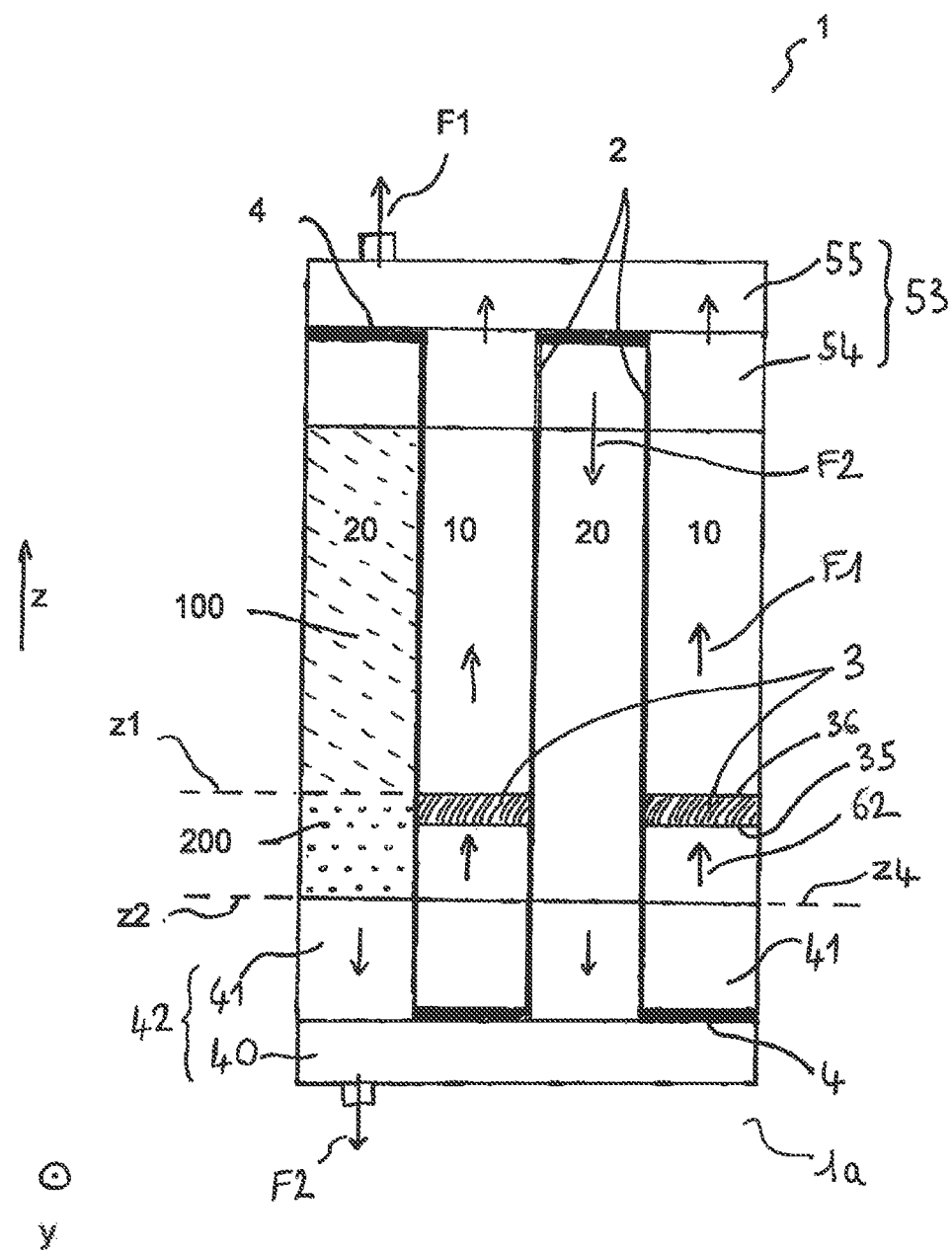
FIG. 4 is another diagrammatic cross-section view, in a plane parallel to that of FIG. 3 but in a direction opposite to that of FIG. 3, of series of passages of the heat exchanger of FIG. 1 in another embodiment of the invention.

In the depictions of FIGS. 1, 3 and 4, the semi-tubular collectors 50, 45 serve for introduction of the fluids into the exchanger 1, and the semi-tubular collectors 40, 55 serve for evacuation of these fluids from the exchanger 1.

In this variant embodiment, the collector supplying one of the fluids and the collector evacuating the other fluid are situated at a same end of the exchanger, the fluids F1, F2 thus circulating in countercurrent in the exchanger 1.

In another variant embodiment, the frigorigenic and calorigenic fluids may also circulate in co-current, the means for supply of one of the fluids and the means for evacuating the other fluid then being situated at opposite ends of the exchanger 1.

Preferably, the longitudinal axis is vertical when the exchanger 1 is in operation. The frigorigenic fluid F1 globally flows vertically in the ascending direction. Other orientations and flow directions of the fluids F1, F2 are naturally possible without leaving the scope of the present invention.

It should be noted in the context of the invention that one or more frigorigenic fluids F1 and one or more calorigenic fluids F2 of different natures may flow within the passages 10, 20 of the first and second series of the same exchanger.

The distribution and evacuation means 42, 43, 52, 53 advantageously comprise distribution waves 41, 44, 51, 54 arranged between two successive plates 2, in the form of undulating sheets which extend from the inlet and outlet openings. The distribution waves 41, 44, 51, 54 ensure the uniform distribution and recovery of fluids over the entire width of the passages 10, 20.

Also, the passages 10, 20 advantageously comprise heat exchange structures arranged between the plates 2. The function of the structures is to increase the heat exchange area of the exchanger. In fact, the heat exchange structures are in contact with the fluids circulating in the passages and transfer heat flows by conduction to the adjacent plates 2 to which they may be fixed by brazing, which increases the mechanical strength of the exchanger.

The heat exchange structures thus serve as cross-braces between the plates 2, in particular on assembly of the exchanger by brazing, and to prevent any deformation of the plates on use of pressurised fluids. They also guide the flow of the fluid in the exchanger passages.

Preferably, these structures comprise heat exchange waves 11 which advantageously extend in the width and length of the passages 10, 20 parallel to the plates 2, in the extension of the distribution waves 41, 44, 51, 54 in the length of the passages 10, 20. Thus the majority of the length of the passages 10, 20 of the exchanger forms the actual heat exchange part which is equipped with a heat exchange structure, said main part being edged by distribution parts equipped with distribution waves 41, 44, 51, 54.

FIG. 1 illustrates a passage 10 of the first series configured to distribute a frigorigenic fluid F1 in the form of a two-phase gas/liquid mixture. The frigorigenic fluid F1 is separated in a separating device 6 into a liquid phase 61 and a gaseous phase 62, which are introduced separately into the exchanger 1 via a lateral collector 30 and the collector 50. The two phases 61, 62 are then mixed together by means of the mixing device 3 which is arranged in the passage 10 and depicted diagrammatically on FIG. 1. Advantageously, several passages 10 or all passages 10 of the first series comprise a mixing device 3.

According to a variant embodiment, the mixing device 3 comprises separate inlets 31, 32 for the liquid or gaseous phases of the frigorigenic fluid F1. Said separate inlets 31, 32 are fluidically connected via a common mixing volume to at least one outlet 33 for a two-phase liquid/gas mixture. The inlets 31, 32 and/or the outlet 33 may open at the end faces 35, 36 of the mixing device 3, or be recessed towards the interior of the device 3 relative to said faces 35, 36.

Figure 2A:
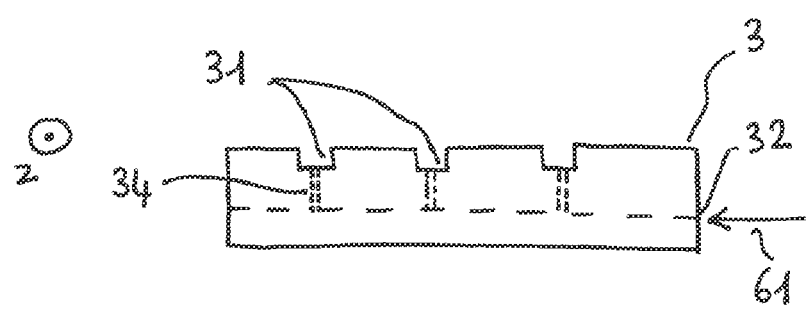
FIGS. 2A and 2B are diagrammatic cross-section views, in two planes perpendicular to that of FIG. 1, illustrating an exemplary structure and operation of the mixing device of an exchanger according to FIG. 1.
Figure 2B:
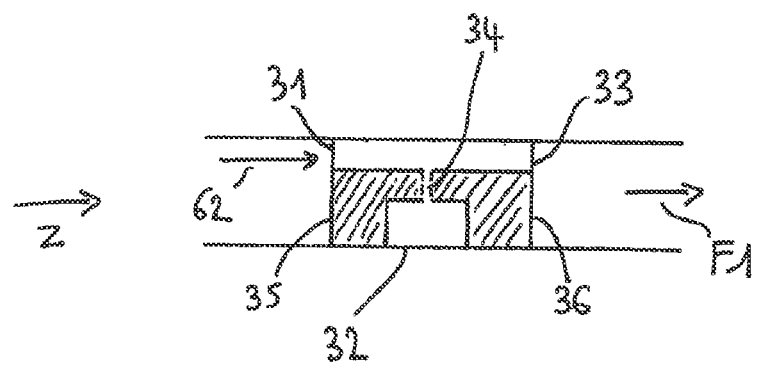

In the embodiment illustrated on FIGS. 2A and 2B, the mixing device 3 is a bar or rod which extends in the width of the passage 10. The bar 3 comprises grooves 31, 32 machined perpendicularly to each other and connected by holes 34.

In the depictions of FIGS. 1, 2A and 2B, the gaseous phase 62 is introduced into a row of grooves 31 arranged parallel to the longitudinal axis z, and the liquid phase 61 is introduced into at least one groove 32 extending parallel to the transverse axis y.

According to another embodiment (not shown), the mixing device 3 may comprise one or more tubes in which a phase of the frigorigenic fluid F1 is introduced, this phase emerging from the tube or tubes via orifices drilled in their wall. The other phase is introduced upstream of the tube or tubes and flows around these tubes.

Naturally, the points for introduction of the liquid phase 61 and gaseous phase 62 into the exchanger may be reversed relative to the depictions given on the figures.

FIG. 3 is a diagrammatic cross-section view, in a plane parallel to the longitudinal axis z and perpendicular to the lateral axis y, of the exchanger FIG. 1. There we see a stack of passages 10, 20 of the first and second series, represented by a number limited to 4 for reasons of simplification.

According to the invention, a heat exchange structure is housed in at least one passage 20 adjacent to the passage 10 containing the mixing device 3. This heat exchange structure is divided along the longitudinal axis z into at least a first portion 100 and a second portion 200, the second portion 200 extending facing at least part of the mixing device 3. The first and second portions 100, 200 are juxtaposed along the longitudinal axis z of the exchanger 1, i.e. positioned end to end as illustrated on FIGS. 3 and 4. In other words, the first and second portions 100, 200 succeed each other or are situated one immediately next to the other along the axis z.

The term "facing" means "opposite" or "at the level of" the mixing device 3. In other words, at least part of the second portion 200 is situated along axis z at a position at which a part of the mixing device 3 is also situated.

According to the invention, the second portion 200 is configured so as to present a heat exchange coefficient which is lower than the heat exchange coefficient of the first portion 100.

By positioning a structure of low thermal efficacy in a part of the adjacent passage situated at the level of the mixing device, the exchanges of heat which may take place with the calorigenic fluid, at the level of the inlet points of the liquid and gaseous phases of the frigorigenic fluid into the exchanger, are hugely reduced. This allows limitation or even avoidance of vaporisation of the liquid phase of the frigorigenic fluid before it is mixed with the gaseous phase of said frigorigenic fluid. The two phases of the mixture are thus distributed as homogenously as possible inside the passages for the two-phase mixture, and between the different passages for the two-phase mixture.

This solution has the advantages of being simple to implement, of not changing the size of the exchanger and not complicating its structure. Also, the heat exchange structure according to the invention allows a reduction in the transfer of heat towards the mixing device without weakening the mechanical strength of the exchanger, since the function of cross-bracing between the plates 2 continues to be provided by the second portion 200.

The term "heat exchange coefficient" or "heat transfer coefficient" means a coefficient quantifying the flow of energy through the heat exchange structure per unit of surface area, volume or length.

The heat exchange coefficient can be defined as follows (in the case for superficial heat transfer):

$$h = \frac{\Delta Q}{A \cdot \Delta T \cdot \Delta t}$$

where:
h: heat exchange coefficient expressed in Watts per square metre Kelvin ($W \cdot m^{-2} \cdot K^{-1}$),
$\Delta Q$: energy transferred in Joules (J),
A: exchange area in square metres ($m^2$),
$\Delta T$: temperature difference on either side of the exchange area in Kelvin or degrees Celsius (K or °C.),
$\Delta t$: time interval in seconds (s).

The heat transfer coefficient of a structure depends on intrinsic parameters, i.e. specific to the exchange structure itself, in particular the density of the wave forming the structure and the thickness of the wave structure, and on extrinsic parameters, i.e. specific to the process implemented, in particular the flow of fluids and the temperature difference between the fluids. The heat transfer coefficient is given by the Nusselt number (Nu) via the following equation:

$$Nu = \frac{h \cdot L_c}{k}$$

where:
h: heat transfer coefficient,
$L_c$: characteristic length,
k: thermal conductivity of the fluid.

Numerous empirical correlations supply an equation for calculating the Nusselt number from which the heat transfer coefficient can be extracted.

In particular, the heat exchange coefficient of a structure may be determined, in the case of a monophase liquid and gas fluid, by the Nusselt number calculated from the relationship below:

$$Nu = CjRePr^{1/3}$$

where Nu: Nusselt number
Cj: Colburn factor
Re: Reynolds number
Pr: Prandtl number.

In the case of a diphasic liquid-gas mixture, the heat exchange coefficient may be determined using correlation methods known in themselves.

In the context of the invention, the heat exchange coefficient of the second portion 200, and the heat exchange coefficient of the first portion 100 are compared using identical or quasi-identical methods of theoretical determination or measurement, since the conditions specific to the exchange process (i.e. extrinsic parameters) are identical or quasi-identical.

Preferably, such a heat exchange structure is housed in several or in all passages 20 which are adjacent to passages 10 containing a mixing device 3. Said structure extends over almost all or over all of the width of the passages 20 in axis y, such that the structure is advantageously in contact with each plate 2 forming the passage 20.

According to an advantageous embodiment of the invention, said first and second portions 100, 200 of the heat exchange structure respectively comprise a first wave structure and a second wave structure 100, 200. The wave structures 100, 200 each comprise several wave fins 123, 223 or legs 123, 223 connected alternately by wave peaks 121, 221 and wave troughs 122, 222 succeeding each other in undulation directions D1, D2. The second wave structure 200 extends facing at least part of the mixing device 3 and has a density which is less than the density of the first wave structure. The reduction in density of the second wave structure 200 allows a reduction in the exchange area of the structure facing the mixing device, which allows a reduction in the heat exchanges by convection between the fluid circulating in the mixing device and in the adjacent passage of the second series.

Preferably, the density of the second wave structure represents between 10% and 90%, preferably between 20% and 80%, further preferably between 25% and 50% of the density of the first wave structure.

In the context of the invention, the density of each wave structure 100, 200 is defined as the number of wave fins 123, 223 per unit of length measured in the respective undulation directions D1, D2. To measure the density of a wave structure, generally a given wave length in its undulation direction is considered, and the number of wave fins present on this length is determined, or on a multiple of this length with subsequent division by said multiple for greater precision. In general, the length considered is 1 inch or 2.54 cm. We therefore speak of the number of wave fins per 2.54 cm or the number of legs per 2.54 cm.

Figure 5A:
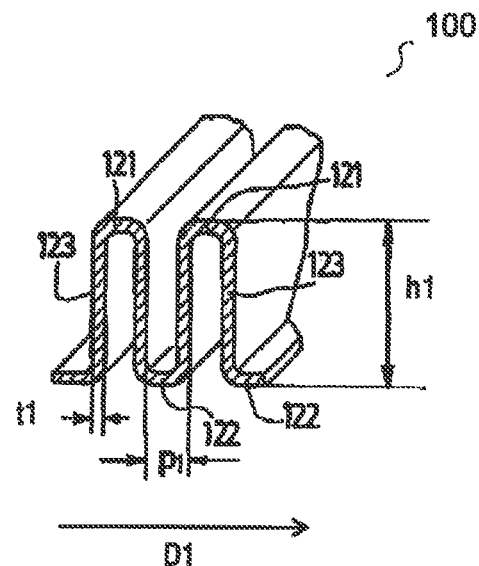
FIGS. 5A and 5B are diagrammatic cross-section views of portions of the heat exchange structure according to one embodiment of the invention.
Figure 5B:
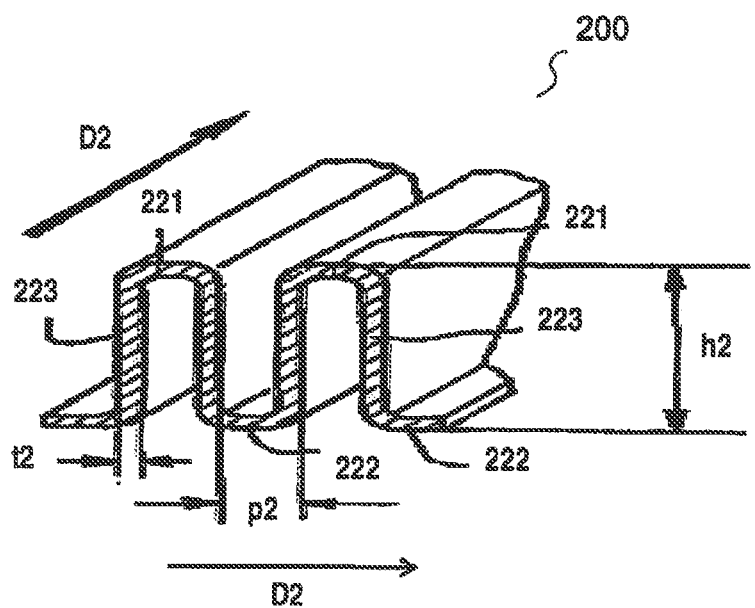

With reference to FIGS. 5A and 5B, the second wave structure 200 therefore has a distance p2 between two successive wave fins 223 which is greater than the distance p1 between two successive wave fins 123 of the first wave structure 100.

Preferably, the density of the second wave structure 200 is between 6 and 15 fins per 2.54 centimetres, i.e. 6 and 15 fins per inch.

With regard to the density of the first wave structure 100, this may lie between 15 and 30 fins per 2.54 centimetres, i.e. 15 and 30 fins per inch, preferably between 18 and 25 fins per 2.54 centimetres, i.e. 18 and 25 fins per inch.

FIGS. 5A and 5B illustrate exemplary embodiments in which the wave fins 123, 223 and the wave troughs 122, 22 form, in cross-section, rectilinear segments which are mutually parallel, the wave fins 123, 223 being situated in planes perpendicular to directions D1, D2. Alternatively, the waves 100, 200 may have a cross-section of sinusoidal, triangular or any other suitable form.

Advantageously, the first and second portions 100, 200 are each formed from one or more strips, i.e. fine metal sheets preferably formed from aluminium or an aluminium alloy. These strips have thicknesses preferably lying between 0.2 and 0.6 mm.

In a particular embodiment, the second portion 200 is formed from a strip with a thickness which is greater than the thickness of the strip forming the first portion 100. This allows a reduction in the density of the second portion 200 while giving it a sufficient rigidity to ensure the good mechanical strength of the exchanger.

In the context of the invention, the first and second wave structures may have heights h1, h2 typically between 3 and 10 mm. Preferably, the heights h1, h2 are selected such that the first and second wave structures 100, 200 extend over almost all or over all of the width of the passage 200 in the transverse direction y.

Preferably, the first wave structure 100 and/or the second wave structure 200 are arranged in the passages 10, 20 of the first and second series such that their undulation directions D1, D2 are globally parallel to the direction of flow of the fluids in the passages 10, 20 (an arrangement known as "easy way"). Such an arrangement offers better control of the process and greatly limits the risk of blockage of the exchange passages. Thus, with a vertical arrangement of the exchanger 1 as shown in FIGS. 3 and 4, the wave structures 100, 200 are waves with vertical generatrix.

It is also possible that the first wave structure 100 and/or the second wave structure 200 are arranged such that the undulation directions D1, D2 are globally perpendicular to the direction of flow of the fluids (an arrangement known as "hard way"). As depicted on FIGS. 3 and 4, the wave structures 100, 200 are then waves with horizontal generatrix.

Different types of wave structure normally used in heat exchangers of the brazed plate and fin type may be used to form the first and second wave structures 100, 200. The wave structures may be selected from the types of waves known as straight waves, serrated waves, undulating waves or herringbone waves, perforated or otherwise.

As a first wave structure, advantageously a serrated or herringbone wave is used. This type of wave allows creation of turbulence in the flow of the calorigenic fluid F2, which has the effect of increasing the heat exchange coefficient of the wave structure.

As the second wave structure, advantageously a straight wave or perforated straight wave is used, this type of wave creating less turbulence in the fluid flow and consequently being thermally less efficient.

The first portion 100 is advantageously situated downstream of the first portion 200 in a direction parallel to the direction of flow of the frigorigenic fluid F1 in the passage 10, as shown on FIGS. 3 and 4. Preferably, the second portion 200 extends facing the entirety of the mixing device 3. It may also extend beyond the one and/or the other of the end faces 35, 36 of the mixing device 3. Advantageously, the second portion 200 extends at least beyond the end face 35 via which the liquid or gaseous phase of the frigorigenic fluid F1 is supplied, as shown on FIG. 4.

In this way, the heat exchanges which may take place between the calorigenic fluid F2 circulating in the adjacent passage 20 and the liquid phase of the frigorigenic fluid F1 before it mixes with the gaseous phase, are reduced as far as possible.

Thus, in the depiction shown on the figures, the second portion 200 extends downstream of the mixing device 3 in the direction of flow of the calorigenic fluid F2 during operation of the exchanger.

The mixing device 3 may have a length parallel to the longitudinal axis z of between 30 and 80 mm.

Preferably, the second portion 200 has a length parallel to the longitudinal axis z which is at least equal to the length of the mixing device 3. The second portion 200 may have a length parallel to the longitudinal axis z which is between 30 and 300 mm.

As explained above, the exchanger 1 comprises distribution and evacuation means 42, 43, 52, 53 configured for distributing the different fluids selectively into the passages 10, 20 and for evacuating said fluids from said passages 10, 20.

In particular, the exchanger 1 may comprise, at one end 1a which is situated in the lower part of the exchanger in the case where the exchanger is operating in the vertical position and the frigorigenic fluid F1 is circulating in the ascending direction (as shown on FIGS. 1, 3, and 4), second means 52 for distributing a liquid or gaseous phase of the frigorigenic fluid F1 into the passage or passages 10.

The same end 1a also comprises the first means 42 which may, depending on case, be means for distributing or evacuating the calorigenic fluid F2 into or from said at least one passage 20.

In the flow configuration illustrated on FIGS. 1, 3 and 4 in which the fluids F1, F2 circulate in countercurrent, the first means 42 are the means for evacuating the calorigenic fluid F2.

As depicted on FIGS. 3 and 4, said at least one outlet 33 for the mixture of the liquid phase 61 and gaseous phase 62 is situated in the longitudinal axis z at a first position z1 in the passage 10 of the first series.

Advantageously, the second portion 200 extends at least from the first position z1 to a second position z2 situated between the first position z1 and the first means 42 for distributing or evacuating the calorigenic fluid F2. In this way, the quantity of heat which may be transferred from the calorigenic fluid F2 to the one or the other of the two phases before these are mixed by the device 3, is limited as far as possible, and the exchanges of heat between the fluids upstream of the device 3 once the two phases have been mixed, i.e. in the main part of the length of the exchanger constituting the actual heat exchange part, is promoted.

Thus the first portion 100 advantageously extends parallel to axis z between the second portion 200 and the second means 53 for evacuating the frigorigenic fluid F1.

In a particular embodiment, the position z2 may correspond to the position of the inlet 31 for the one or the other of the phases of the frigorigenic fluid F1 along the axis z.

In particular, the position z1 may correspond to the position of the end face 36 of the mixing device 3, and/or the position z2 may correspond to the position of the end face 35 of the mixing device 3.

Advantageously, the second portion 200 extends parallel to axis z up to the first means 42 for distributing or evacuating the calorigenic fluid F2.

In particular, the second portion 200 may be formed by all or part of said first means 42 for distributing or evacuating the calorigenic fluid F2.

In the case where the heat exchange structure comprises a second portion 200 formed from a wave structure 200, the wave structure 200 is advantageously formed by an extension of the distribution wave 41 in the main part of the length of the exchanger constituting the actual heat exchange part.

In a variant embodiment illustrated on FIG. 3, the heat exchange structure may also be divided in the longitudinal direction z into a third portion 300, the second portion 200 being arranged between the first portion 100 and the third portion 300.

According to the invention, the second portion 200 is configured so as to present an exchange coefficient which is lower than the heat exchange coefficient of the third portion 300. In particular, the third portion 300 may comprise a third wave structure 300 with characteristics identical to those of the second wave structure 200.

Naturally, the invention is not limited to the specific examples described and illustrated in the present application. Further variants or embodiments within the reach of the person skilled in the art may also be considered without leaving the scope of the invention.

For example, in the configuration of the exchanger illustrated on the figures, the liquid phase of the fluid F1 is injected laterally and the gaseous phase is injected at the lower end of the exchanger. Other injection configurations are naturally conceivable, depending on the proportion of liquid to gas in the two-phase mixture or depending on the constraints imposed by the process to be implemented. Thus, it is possible to inject the gaseous phase laterally upstream or downstream of the lateral injection point of the liquid phase.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A heat exchanger comprising:
   a plurality of plates arranged parallel to each other so as to define a first series of passages for conducting at least one frigorigenic fluid and a second series of passages for conducting at least one calorigenic fluid to be brought into a heat exchange relationship with at least said frigorigenic fluid, each passage being defined between two successive plates and extending parallel to a longitudinal axis, and
   at least one mixing device arranged in at least one passage of the first series, said mixing device being configured to receive a liquid phase and a gaseous phase of the frigorigenic fluid and to distribute a mixture of said phases into said at least one passage,
   at least one passage of the second series adjacent to said at least one passage of the first series containing a heat exchange structure divided in the longitudinal direction into at least a first portion and a second portion which are juxtaposed along the longitudinal axis, the second portion extending facing at least part of the mixing device,
   wherein the second portion is configured so as to present a heat exchange coefficient which is lower than the heat exchange coefficient of the first portion.

2. The heat exchanger according to claim 1, wherein said first and second portions comprise respectively at least one first wave structure and at least one second wave structure, said first and second wave structures being juxtaposed along the longitudinal axis and each having several wave fins connected alternately by wave peaks and by wave troughs succeeding each other in an undulation direction, the second wave structure extending facing at least part of the mixing device and being configured so as to present a heat exchange coefficient which is lower than the heat exchange coefficient of the first wave structure.

3. The heat exchanger according to claim 2, wherein the second wave structure has a density which is lower than the density of the first wave structure, the density of each wave structure being defined as the number of wave fins per unit of length measured in the undulation direction.

4. The heat exchanger according to claim 3, wherein the density of the second wave structure represents between 20% and 80% of the density of the first wave structure.

5. The heat exchanger according to claim 3, wherein the density of the second wave structure is between 6 and 15 fins per inch.

6. The heat exchanger according to claim 1, wherein said first and second portions are formed from strips, the second portion being formed from at least one strip with a thickness which is greater than the thickness of at least one strip forming said first wave structure of the portion.

7. The heat exchanger according to claim 2, wherein the second wave structure is a straight wave, the first wave structure being selected from a straight wave, a straight perforated wave, a serrated wave, an undulating wave or a herringbone wave.

8. The heat exchanger according to claim 1, wherein the second portion extends at least facing the entirety of the mixing device.

9. The heat exchanger according to claim 1, wherein the second portion has a length parallel to the longitudinal axis of between 30 and 500 mm.

10. The heat exchanger according to claim 1, wherein the heat exchange structure is furthermore divided along the longitudinal axis into a third portion, the second portion being configured so as to present a heat exchange coefficient which is less than or equal to the heat exchange coefficient of the third portion, the second portion being arranged between the first portion and the third portion.

11. The heat exchanger according to claim 1, wherein at a same end of the exchanger, the heat exchanger comprises first means for distributing or evacuating calorigenic fluid into or from said at least one passage of the second series of passages, and second means for distributing a liquid or gaseous phase of the frigorigenic fluid into said at least one passage of the first series towards the mixing device.

12. The heat exchanger according to claim 1, wherein the mixing device comprises separate inlets for a liquid phase and a gaseous phase of the frigorigenic fluid, said separate inlets being connected fluidically via a common mixing volume to at least one outlet for a mixture of said liquid and gaseous phases.

13. The heat exchanger according to claim 12, wherein the outlet for a two-phase liquid/gas mixture of the mixing device is situated along the longitudinal axis at a first position in said at least one passage of the first series, the second portion extending at least from the first position up to a second position situated between the first position and the first means for distributing or evacuating the calorigenic fluid.

14. The heat exchanger according to claim 13, wherein the second portion extends up to the first means for distributing or evacuating the calorigenic fluid.

15. The heat exchanger according to claim 12, wherein the second portion is formed by all or part of said first means for distributing or evacuating the calorigenic fluid.

16. The heat exchanger according to claim 3, wherein the density of the second wave structure represents between 25% and 50% of the density of the first wave structure.

* * * * *